US012279812B2

(12) United States Patent
Shelton et al.

(10) Patent No.: US 12,279,812 B2
(45) Date of Patent: Apr. 22, 2025

(54) LASER FIBER VARYING LATERAL POSITION AND INTENSITY

(71) Applicant: GYRUS ACMI, INC., Southborough, MA (US)

(72) Inventors: Kurt G. Shelton, Bedford, MA (US); Masayasu Chida, Tokyo (JP); Sergey A. Bukesov, Acton, MA (US); Brian M. Talbot, Southborough, MA (US); Vladimir Polejaev, Middletown, CT (US)

(73) Assignee: Gyrus ACMI, Inc., Westborough, MA (US)

( * ) Notice: Subject to any disclaimer, the term of this patent is extended or adjusted under 35 U.S.C. 154(b) by 122 days.

(21) Appl. No.: 16/984,440

(22) Filed: Aug. 4, 2020

(65) Prior Publication Data

US 2021/0038307 A1   Feb. 11, 2021

Related U.S. Application Data

(60) Provisional application No. 63/027,007, filed on May 19, 2020, provisional application No. 63/005,570, (Continued)

(51) Int. Cl.
*A61B 18/20* (2006.01)
*A61B 18/22* (2006.01)
(Continued)

(52) U.S. Cl.
CPC .... *A61B 18/22* (2013.01); *A61B 2017/00402* (2013.01); *A61B 2018/00505* (2013.01); (Continued)

(58) Field of Classification Search
CPC ............... A61B 18/20; A61B 2018/20; A61B 2018/2238; A61N 5/06
See application file for complete search history.

(56) References Cited

U.S. PATENT DOCUMENTS

| 4,887,600 A | 12/1989 | Watson et al. |
| 4,967,416 A | 10/1990 | Esterowitz et al. |
| (Continued) | | |

FOREIGN PATENT DOCUMENTS

| CN | 101420898 | 4/2009 |
| CN | 101909512 | 12/2010 |
| (Continued) | | |

OTHER PUBLICATIONS

Physik Instrumente (PI) "Displacement Modes of Piezoelectric Actuators" (Year: 2023).*

(Continued)

*Primary Examiner* — Lynsey C Eiseman
(74) *Attorney, Agent, or Firm* — Schwegman Lundberg & Woessner, P.A.

(57) ABSTRACT

A lithotripsy or other medical laser treatment system can include a lateral actuator to laterally displace a distal portion of a laser fiber, such as can be scanned or otherwise controlled to generate a spatial or spatiotemporal sub-targeting pattern without requiring laterally moving an endoscope carrying the laser fiber in a longitudinal passage such as a working channel. A targeted stone can be selectively weakened along the pattern, such as using lower energy pulses, before being fragmented, such as by a higher energy shock pulse.

35 Claims, 9 Drawing Sheets

Related U.S. Application Data filed on Apr. 6, 2020, provisional application No. 62/882,837, filed on Aug. 5, 2019.

(51) Int. Cl.
  A61B 17/00     (2006.01)
  A61B 18/00     (2006.01)
  A61B 90/30     (2016.01)

(52) U.S. Cl.
  CPC ............... *A61B 2018/20355* (2017.05); *A61B 2018/20357* (2017.05); *A61B 2018/205547* (2017.05); *A61B 2018/2238* (2013.01); *A61B 2090/309* (2016.02)

(56) References Cited

U.S. PATENT DOCUMENTS

| | | | |
|---|---|---|---|
| 5,621,745 | A | 4/1997 | Yessik et al. |
| 6,554,824 | B2 | 4/2003 | Davenport et al. |
| 9,017,316 | B2 | 4/2015 | Khatchaturov et al. |
| 9,445,871 | B2 | 9/2016 | Kang et al. |
| 9,486,286 | B2 | 11/2016 | Hodel et al. |
| 9,561,078 | B2 * | 2/2017 | Seibel .................. A61B 1/0017 |
| 9,757,199 | B2 | 9/2017 | Chia et al. |
| 9,949,615 | B2 | 4/2018 | Zappia et al. |
| 9,968,403 | B2 | 5/2018 | Hasenberg et al. |
| 10,039,604 | B2 | 8/2018 | Chia et al. |
| 10,067,304 | B2 | 9/2018 | Yu et al. |
| 10,105,184 | B2 | 10/2018 | Beck et al. |
| 10,175,435 | B2 | 1/2019 | Peng et al. |
| 10,258,415 | B2 | 4/2019 | Harrah et al. |
| 10,383,690 | B2 | 8/2019 | Hodel et al. |
| 2001/0055462 | A1 | 12/2001 | Seibel |
| 2003/0083607 | A1 * | 5/2003 | Bobo, Jr. .............. A61B 18/24 606/7 |
| 2006/0217688 | A1 | 9/2006 | Lai |
| 2008/0058629 | A1 | 3/2008 | Seibel et al. |
| 2008/0249369 | A1 * | 10/2008 | Seibel .................. G02B 23/2476 600/182 |
| 2009/0028407 | A1 | 1/2009 | Seibel et al. |
| 2010/0282954 | A1 | 11/2010 | Hendriks et al. |
| 2014/0194692 | A1 | 7/2014 | Yoshino et al. |
| 2014/0221826 | A1 * | 8/2014 | Joos .................. A61B 18/20 600/425 |
| 2015/0080719 | A1 | 3/2015 | Wheatley |
| 2015/0173622 | A1 * | 6/2015 | Parto .................. A61B 18/20 600/478 |
| 2015/0224249 | A1 | 8/2015 | Ciulla et al. |
| 2015/0230864 | A1 | 8/2015 | Xuan et al. |
| 2015/0257832 | A1 | 9/2015 | Ebata |
| 2015/0272674 | A1 | 10/2015 | Xuan et al. |
| 2015/0272679 | A1 * | 10/2015 | Wang .................. A61B 18/24 606/15 |
| 2015/0289937 | A1 | 10/2015 | Chia et al. |
| 2015/0320307 | A1 | 11/2015 | Wheatley |
| 2016/0081749 | A1 | 3/2016 | Zhang et al. |
| 2016/0166319 | A1 | 6/2016 | Yu et al. |
| 2017/0311779 | A1 | 11/2017 | Nakajima |
| 2018/0092693 | A1 | 4/2018 | Falkenstein et al. |
| 2019/0113700 | A1 | 4/2019 | Peng et al. |
| 2019/0151022 | A1 | 5/2019 | Yu et al. |
| 2019/0159839 | A1 | 5/2019 | Zhang et al. |
| 2019/0192237 | A1 | 6/2019 | Harrah et al. |
| 2019/0246908 | A1 | 8/2019 | Pyun et al. |
| 2019/0282299 | A1 | 9/2019 | Fan et al. |
| 2019/0298449 | A1 | 10/2019 | Khachaturov et al. |
| 2019/0393669 | A1 | 12/2019 | Yu et al. |

FOREIGN PATENT DOCUMENTS

| | | |
|---|---|---|
| CN | 104619281 | 5/2015 |
| CN | 105531611 | 4/2016 |
| CN | 105852787 | 8/2016 |
| CN | 106028910 | 10/2016 |
| CN | 107072469 | 8/2017 |
| CN | 114206250 A | 3/2022 |
| DE | 112020003743 T5 | 4/2022 |
| EP | 3510962 A1 | 7/2019 |
| EP | 3512448 A1 | 7/2019 |
| EP | 3522811 A1 | 8/2019 |
| JP | 2001190565 | 7/2001 |
| JP | 2003535659 A | 12/2003 |
| JP | 2004321792 A | 11/2004 |
| JP | 2009516568 A | 4/2009 |
| JP | 2013081680 | 5/2013 |
| JP | 2014097123 | 5/2014 |
| JP | 2022544128 A | 10/2022 |
| JP | 7479448 | 5/2024 |
| JP | 2024091862 | 7/2024 |
| WO | WO-1990014797 A1 | 12/1990 |
| WO | WO-2018119285 A1 | 6/2018 |
| WO | WO-2020033121 A1 | 2/2020 |
| WO | WO-2021026136 A1 | 2/2021 |

OTHER PUBLICATIONS

"Indian Application Serial No. 202247003230, First Examination Report mailed Jun. 23, 2022", 6 pgs.

"International Application Serial No. PCT/US2020/044858, International Preliminary Report on Patentability mailed Feb. 17, 2022", 8 pgs.

"International Application Serial No. PCT/US2020/044858, International Search Report mailed Nov. 9, 2020", 5 pgs.

"International Application Serial No. PCT/US2020/044858, Written Opinion mailed Nov. 9, 2020", 6 pgs.

Bosschaart, Nienke, et al., "A literature review and novel theoretical approach on the optical properties of whole blood", Lasers Med Sci, (2014), 453-479.

Jacques, Steven, "Optical Absorption of Carbonized Tissue", [Online]. Retrieved from the Internet: <URL: https://omlc.org/spectra/carbon/>, (2018), 3 pgs.

Vinnichenko, Victoriya, et al., "Comparison of a novel high-power blue diode laser ($\lambda$=442 nm) with Ho:YAG ($\lambda$=2100 nm), Tm fiber ($\lambda$=1940 nm), and KTP ($\lambda$=532 nm) lasers for soft tissue ablation", Proc. SPIE 10468, Therapeutics and Diagnostics in Urology, [Online]. Retrieved from the Internet: <URL: https://www.researchgate.net/publication/323002187>, (Feb. 2018), 8 pgs.

"Indian Application Serial No. 202247003230, Response Filed Dec. 15, 2022 to First Examination Report mailed Jun. 23, 2022", 23 pgs.

"Japanese Application Serial No. 2022-507468, Notification of Reasons for Refusal mailed May 9, 2023", w/ English Translation, 11 pgs.

"Japanese Application Serial No. 2022-507468, Response filed Jul. 28, 2023 to Notification of Reasons for Refusal mailed May 9, 2023", w/ english claims, 13 pgs.

"Chinese Application Serial No. 202080056068.5, Office Action mailed Sep. 21, 2023", W English Translation, 31 pgs.

"Japanese Application Serial No. 2022-507468, Final Notification of Reasons for Rejection mailed Oct. 31, 2023", W English Translation, 7 pgs.

"Chinese Application Serial No. 202080056068.5, Response filed Jan. 18, 2024 to Office Action mailed Sep. 21, 2023", w/ english claims, 11 pgs.

"Japanese Application Serial No. 2022-507468, Repsonse filed Jan. 9, 2024 to Final Notification of Reasons for Rejection mailed Oct. 31, 2023", w english claims, 11 pgs.

"Chinese Application Serial No. 202080056068.5, Office Action mailed Mar. 21, 2024", w English translation, 29 pgs.

"Chinese Application Serial No. 202080056068.5, Response filed May 10, 2024 to Office Action mailed Mar. 21, 2024", w current English claims, 11 pgs.

"Chinese Application Serial No. 202080056068.5, Decision of Rejection mailed Jun. 7, 2024", W English Translation, 32 pgs.

"Indian Application Serial No. 202247003230, Hearing Notice mailed Jun. 20, 2024", 2 pgs.

"Indian Application Serial No. 202247003230, Response filed Jul. 23, 2024 to Hearing Notice mailed Jun. 20, 2024", w claims, 12 pgs.

(56) References Cited

OTHER PUBLICATIONS

"Chinese Application Serial No. 202080056068.5, Request for Reexamination filed Aug. 9, 2024", W English Claims, 12 pgs.

* cited by examiner

# LASER FIBER VARYING LATERAL POSITION AND INTENSITY

CLAIM OF PRIORITY

This application claims the benefit of priority under 35 U.S.C. § 119 (e) of U.S. Provisional Patent Application Ser. No. 62/882,837, filed on Aug. 5, 2019, and U.S. Provisional Patent Application Ser. No. 63/000,570, filed on Mar. 27, 2020, which are herein incorporated by reference in their entireties.

TECHNICAL FIELD

This document relates generally to endoscopic laser systems, and more specifically relates to systems and methods for varying lateral position of a laser fiber and intensity of laser pulses.

BACKGROUND

In laser lithotripsy, pulses of laser energy can be endoscopically applied via a laser fiber to a target, such as a kidney, biliary, gallbladder, or other stone, such as to fragment the stone into various pieces. However, the various resulting pieces can scatter in the body. The resulting pieces can be too large to dissolve or to naturally pass through the body, and can require physician retrieval, such as using a suction device, a forceps, a basket, or another retriever device. Retrieving stone fragments can be extremely time consuming and difficult. The presence and nature of any resulting stone fragments may introduce further challenges for the patient.

SUMMARY

This document describes, among other things, a laser therapy system, such as a lithotripsy system, or other medical treatment system that can include a laser fiber that can be configured for providing one or both of varying lateral position and varying laser pulse intensity. A distal end of the laser fiber can be scanned or otherwise actuated to vary a lateral position of the laser fiber, such as with respect to a central or other reference longitudinal axis of a working lumen or other longitudinal passage of a rigid or flexible endoscope or other elongate medical instruments. In this way, the laser fiber can be re-positioned at one or more of various lateral positions-without requiring moving or re-positioning of the endoscope. At such different lateral positions, laser pulses can be emitted. An intensity of such laser pulses can also be controlled, such as to permit emitting different intensity laser pulses at different lateral positions. The lateral positioning or re-positioning of the laser fiber, the varying of laser pulse intensity, or both of these, can be useful, such as to deliver a sequence or pattern of laser energy to a kidney stone or other stone or other targets. The pattern can be selected to help improve or optimize the way in which the target is treated-such as the way in which the stone is broken up. This can help reduce the size or migration of the resulting fragments of the broken-up kidney stone or other stone or other targets. This, in turn, can help reduce or avoid the need for, or the complexity of, any fragment retrieval by the physician.

Example 1 is a laser therapy system to permit delivering laser energy via an endoscope from different lateral positions without requiring lateral repositioning of the endoscope. The laser therapy system comprises: a laser fiber, including a distal portion that is configured to be inserted into a patient via a longitudinal passage of the endoscope; and wherein the distal portion of the laser fiber is actuatable to be adjustably at least laterally positioned within and with respect to the longitudinal passage at a selected position of a plurality of available laterally displaced positions within the longitudinal passage of the endoscope.

In Example 2, the subject matter of Example 1 optionally includes, wherein the distal portion of the laser fiber includes a bend.

In Example 3, the subject matter of Example 2 optionally includes, wherein the distal portion of the laser fiber is rotatable about the longitudinal passage.

In Example 4, the subject matter of any one or more of Examples 1-3 optionally includes, wherein the laser fiber is configured to be coupled to a laser source controlled by controller circuitry to provide first and second laser pulses via the laser fiber, wherein the second laser pulse includes a higher energy than the first laser pulse, wherein the second pulse is issued laterally closer to a center of a target than when the first laser pulse is issued without requiring lateral repositioning of the endoscope.

In Example 5, the subject matter of any one or more of Examples 1–4 optionally include at least one actuator configured to actuate lateral displacement of the distal portion of the laser fiber in a specified pattern according to a control signal provided by controller circuitry.

In Example 6, the subject matter of Example 5 optionally includes, wherein the distal portion of the laser fiber is further actuatable to be longitudinally translatable with respect to the at least one actuator.

In Example 7, the subject matter of any one or more of Examples 5-6 optionally includes, wherein the at least one actuator comprises: a first actuator configured to actuate lateral displacement of the distal portion of the laser fiber; and a different second actuator configured to actuate longitudinal translation of the laser fiber.

In Example 8, the subject matter of any one or more of Examples 5-7 optionally includes, wherein the controller circuitry is configured to generate the control signal for actuating the at least one actuator using a feedback signal in response to electromagnetic radiation of a target.

In Example 9, the subject matter of Example 8 optionally includes, wherein the feedback signal includes imaging data or spectroscopic data.

In Example 10, the subject matter of any one or more of Examples 8-9 optionally includes, wherein the controller circuitry is configured to generate the control signal for actuating the at least one actuator using information about a distance between a distal end of the laser fiber and the target.

In Example 11, the subject matter of any one or more of Examples 1-10 optionally includes, wherein the distal portion of the laser fiber is at least one of electromagnetically, electrostatically, or piezoelectrically actuatable to be laterally displaced within and with respect to the longitudinal passage when actuated in accordance with a control signal provided by controller circuitry.

In Example 12, the subject matter of any one or more of Examples 1-11 optionally includes, wherein the laser fiber is coupled to a laser source controlled by controller circuitry to provide a lateral pattern of lower energy laser pulses toward a periphery of a target and at least one higher energy laser pulse toward a center of the target, without requiring lateral repositioning of the endoscope.`

In Example 13, the subject matter of Example 12 optionally includes, wherein the lateral pattern includes at least one of a spiral pattern, a serpentine pattern, a star pattern, or a zig-zag pattern.

In Example 14, the subject matter of any one or more of Examples 1-13 optionally includes, wherein the distal portion of the laser fiber is actuatable to be adjustably at least laterally positioned within the longitudinal passage and with respect to a central longitudinal axis of the longitudinal passage at a selected position of a plurality of available laterally displaced positions within the longitudinal passage of the endoscope.

In Example 15, the subject matter of any one or more of Examples 1-14 optionally includes, wherein the distal portion of the laser fiber is actuatable to be adjustably at least laterally positioned within the longitudinal passage and with respect to a central longitudinal axis of the laser fiber at a selected position of a plurality of available laterally displaced positions within the longitudinal passage of the endoscope.

In Example 16, the subject matter of any one or more of Examples 5-10 optionally includes, wherein the at least one actuator is configured to actuate the distal portion of the laser fiber to be adjustably at least laterally positioned within and with respect to the longitudinal passage at a selected position of a plurality of available laterally displaced positions within the longitudinal passage of the endoscope while maintaining the endoscope laterally stationary.

In Example 17, the subject matter of Example 16 optionally includes, wherein the at least one actuator is located at the distal portion of the laser fiber.

In Example 18, the subject matter of any one or more of Examples 16-17 optionally includes, wherein the at least one actuator is located at a proximal portion of the laser fiber.

Example 19 is a method of laser therapy via an endoscope to permit at least laterally re-orienting a laser beam with respect to a target region without requiring moving the endoscope. The method comprises: providing a laser fiber configured to extend through a longitudinal passage of the endoscope; and issuing or receiving a control signal to actuate positioning of a distal portion of the laser fiber at least laterally within the longitudinal passage of the endoscope at a selected position of a plurality of available laterally displaced positions within the longitudinal passage of the endoscope.

In Example 20, the subject matter of Example 19 optionally includes, wherein the laser fiber is actuated by a controller to provide first and second laser pulses via the laser fiber, wherein the second laser pulse includes a higher energy than the first laser pulse.

In Example 21, the subject matter of Example 20 optionally includes, wherein the second laser pulse is issued when the distal portion of the laser fiber is relatively closer to a center of the target region than when the first laser pulse is issued, without requiring lateral repositioning of the endoscope.

In Example 22, the subject matter of any one or more of Examples 20-21 optionally includes, wherein the second laser pulse is issued after a specified time interval of when the first laser pulse is issued, and wherein the first laser pulse is issued repeatedly to consistently apply a first laser pulse energy to a targeted region.

In Example 23, the subject matter of Example 22 optionally includes, wherein the first laser pulse is issued repeatedly while directed along a pattern boundary toward a lateral periphery of a target region, wherein the second laser pulse is applied laterally closer to a center of the target region.

In Example 24, the subject matter of any one or more of Examples 19-23 optionally includes, wherein the distal portion of the laser fiber is laterally displaced in a spiral pattern according to a control signal provided by a controller.

In Example 25, the subject matter of any one or more of Examples 19-23 optionally includes, wherein the distal portion of the laser fiber is laterally displaced in a serpentine pattern according to a control signal provided by a controller.

In Example 26, the subject matter of any one or more of Examples 19-23 optionally includes, wherein the distal portion of the laser fiber is laterally displaced in a zig-zag pattern according to a control signal provided by a controller.

In Example 27, the subject matter of any one or more of Examples 19-23 optionally includes, wherein the distal portion of the laser fiber is laterally displaced in a star pattern according to a control signal provided by a controller.

In Example 28, the subject matter of any one or more of Examples 19-27 optionally includes using information about at least one of a morphology or a composition of at least a portion of the target region to select or control a target pattern including different targeted lateral positions.

In Example 29, the subject matter of any one or more of Examples 19-28 optionally includes issuing or receiving a control signal to actuate the distal portion of the laser fiber to be laterally displaced in a specified pattern to issue one or more laser pulses toward a lateral periphery of a target region before issuing one of more laser pulses closer to a center of the target region.

Example 30 is a laser therapy system for laser therapy via an endoscope to permit at least laterally re-orienting a laser beam toward a target without requiring moving the endoscope, the system comprising: a laser fiber configured to extend through a longitudinal passage of the endoscope; and means for issuing or receiving a control signal to at least laterally position a distal portion of the laser fiber at a selected position of a plurality of available laterally displaced positions within the longitudinal passage of the endoscope.

In Example 31, the subject matter of Example 30 optionally includes, wherein the laser fiber is coupled to a laser source controlled by controller circuitry to provide first and second laser pulses via the laser fiber, wherein the second laser pulse includes a higher energy than the first laser pulse, wherein the second pulse is issued laterally closer to a center of the target than when the first laser pulse is issued, without requiring lateral repositioning of the endoscope.

This summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

In the drawings, which are not necessarily drawn to scale, like numerals may describe similar components in different views. Like numerals having different letter suffixes may represent different instances of similar FIG. 1A illustrates a side sectional view of portions of an endoscope system.

DETAILED DESCRIPTION

This document describes examples of an approach that can help address the problem of controlling stone fragmentation during lithotripsy or other laser surgery or treatment, such as can include using a laser fiber that can be actuated to be laterally positioned or repositioned, such as with respect to an arbitrary reference longitudinal axis of a working channel or other longitudinal passage of an endoscope or other instrument, such as without requiring moving or repositioning the endoscope or other instrument. This can permit multiple pulses or a pattern of multiple pulses to first crack or otherwise prepare the target stone such as at different target locations, intensities, or both, before then fragmenting the stone with a later-delivered laser pulse at a desired location and intensity. This can help permit the stone to fracture in small enough pieces to pass from the body naturally, thereby reducing, minimizing, or avoiding a need for physician intervention for fragment removal.

Figure 1A:
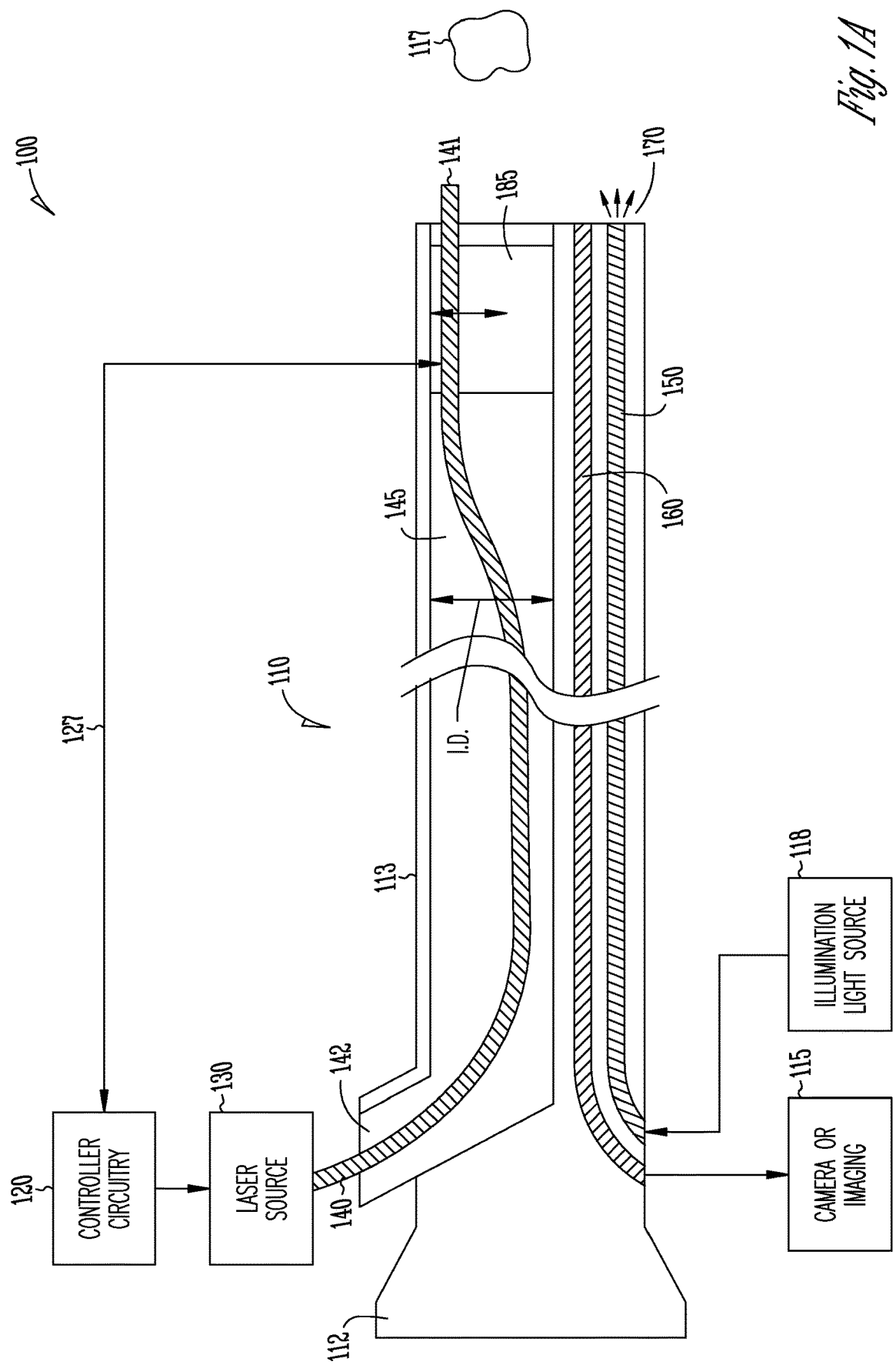
FIG. 1B illustrates an end view of a lateral actuator and laser fiber.
FIG. 1C illustrates an end view of a lateral actuator and laser fiber with a stabilizer.
FIG. 1D illustrates a side sectional view of portions of an endoscope system.
FIGS. 1E-1G illustrate various examples of a side sectional view of portions of an endoscope system.
FIGS. 1H and 1I illustrate examples of a system using a feedback signal reflected from the target to control and adjust the position of the laser fiber with respect to a distal end of an endoscope.

FIG. 1A shows an example of portions of an endoscopic or similar medical treatment system such as an endoscopic laser lithotripsy system 100. In the example of FIG. 1A, the lithotripsy system 100 can include or be coupled to at least one laser source 130. The laser source 130 can be mechanically and optically connected to a laser fiber 140, which can include a single optical fiber or a bundle of optical fibers. The laser fiber 140 can be introduced via a proximal access port 142 to extend within a working channel or other longitudinal passage 145 or lumen of an endoscope 110 or similar instrument. The endoscope 110 can include a proximal handle portion 112 and an elongate distal portion 113 that can be configured to be inserted into a patient, such as via an orifice or incision. The endoscope 110 can be useful for providing visual inspection or treatment of soft (e.g., non-calcified) or hard (e.g., calcified) tissue as well as for visualizing or breaking up or otherwise treating kidney stones or other stones or other targets.

In FIG. 1A, the laser source 130 can include one or more laser sources, such as can include a diode or a diode-pumped thulium fiber laser, holmium laser, green light laser, YAG laser, or other types of laser. The laser source 130 can be configured to provide a variable energy intensity laser output. For example, a lower energy intensity can be used, such as for providing an "aiming" beam or for treating soft (e.g., non-calcified) tissue, and one or more higher energy intensities can be used for providing a "treatment" beam, such as for hard (e.g., calcified) tissue or stones. Multiple higher energy intensity treatment beam levels can be provided, such as on a pulse-by-pulse or target location dependent basis, such as to establish, adjust, or tune a desired treatment pulse energy intensity to a specified level.

In FIG. 1A, the endoscope 110 can include or provide visualization and illumination optics, such as can include a visualization optical pathway 160 and an illumination optical pathway 150, each of which can extend longitudinally along the elongate body 113 of the endoscope 110, such as from a proximal handle 112 portion of the endoscope 110 to a distal end portion of the endoscope 110. An eyepiece or camera or imaging display 115 can be provided at or coupled to the visualization optical pathway 160 such as at or near the proximal handle 112 portion of the endoscope 110, such as can permit user or machine visualization of a target region 117 at or near a distal end of the endoscope 110. Such target region 117 can be illuminated by light 170, such as can be provided by an illumination light source 118 at a proximal end of the illumination optical pathway 150 and emitted from a distal end of the optical illumination pathway 150, or such as can be emitted from an LED or other illumination source that can be located at or near a distal end of the endoscope, such as with electrical conductors extending longitudinally to provide power thereto.

In FIG. 1A, the endoscope 110 can include an elongated distal body portion 113 having a length. The endoscope 110 can include a working channel or longitudinal passage 145 or other lumen extending along its length. The endoscope 110 can be rigid (e.g., rigid when inserted into regions having tissue, the rigid endoscope having sufficient columnar strength for insertion through long tubular anatomy, or the like) or flexible (e.g., flexible such as to follow the contours of tortuous anatomical regions, such as a ureter or biliary area). The working channel or longitudinal passage 145 or other lumen can define a reference longitudinal axis, such as a central longitudinal axis extending therethrough, with the axis being straight when the distal portion 113 of the endoscope 110 is straight, and bent when the distal portion 113 of the endoscope 110 is bent (e.g., in implementations in which the endoscope is flexible). At the distal portion 113 of the endoscope 110, the central longitudinal axis can be defined to extend longitudinally through the working channel or longitudinal passage 145 or other lumen.

The present approach can include providing the capability to position or re-position at least a distal portion of the laser fiber 140 laterally with respect to the longitudinal passage 145, such as with respect to a reference longitudinal axis such as central longitudinal axis of the working channel or longitudinal passage 145 or other lumen of the endoscope 110 through which the laser fiber 140 extends. This can allow a user to view a target region via the visualization optical pathway 160 and position the distal portion of the endoscope 110 within the longitudinal passage 145 with the target stone in view and targeted by the laser fiber 140. Then, different lateral locations of the stone can be targeted such as by positioning or re-positioning the distal portion of the laser fiber 140 laterally at different locations within the working channel or longitudinal passage 145 or other lumen of the endoscope 110 through which the laser fiber 140 extends. For example, this can allow the distal portion of the laser fiber 140 to be selectively positioned at a desired position such as on a grid on an XY plane that can be defined as extending orthogonally to the central longitudinal axis of the longitudinal passage 145 of the distal portion 113 of the endoscope 110.

An actuator 185 can be included, such as for example, can be located at or near the distal end of the endoscope, such as to actuate lateral positioning or re-positioning of a distal portion of the laser fiber 140 within and with respect to the longitudinal passage 145 of the distal portion 113 of the endoscope 110. This can permit scanning or other lateral adjustment of the targeting of the laser fiber 140 without requiring the endoscope 110 to be bent or to be moved laterally. The controller circuitry 120 can be in electrical communication with the actuator 185 such as via an electrical communications bus 127 such as to remotely control the actuator 185 to establish a lateral position of the laser fiber 140. The electrical communications bus 127 can include electrical connections that extend along the laser fiber 140 or electrical connections that extend within the distal portion 113 of the body of the endoscope 110, such as to connect with the actuator 185 or to connect with electrical contacts thereto.

The actuator 185 can be controlled to position or reposition a distal portion of the laser fiber 140 within the longitudinal passage 145 of the distal portion 113 of the endoscope 110, such as to permit delivering laser energy via the endoscope 110 from different lateral positions without requiring lateral repositioning of the endoscope 110. Such positioning or repositioning of a distal portion of the laser fiber 140 is described herein with respect to a longitudinal reference axis such as the central longitudinal axis or other reference longitudinal axis, for conceptual clarity of illustration and explanation. However, such lateral positioning or re-positioning of the distal portion of the laser fiber 140 by the actuator 185 can be with respect to another suitable fixed reference location, including with respect to an inner lateral dimension such as an inner diameter (I.D.) of the longitudinal passage 145 itself.

The actuator 185 can operate to actuate positioning or movement of a distal portion of the laser fiber 140 such as to locate it at a selected lateral position of a plurality of available lateral positions. The movement of the distal portion of the laser fiber 140 can be actuated and conducted without requiring movement of the endoscope 110 or movement of the laser source 130. By allowing the user to maintain visualization of the target region 117 at a given position or location of the endoscope 110 via a stationary visualization pathway 160, precise targeting, re-targeting, or both, by the distal portion of the laser fiber 140 (such as by moving the distal portion of the laser fiber 140 laterally within and with respect to the longitudinal passage 145) can be accomplished together with ease of positioning and targeting for the user.

The actuator 185 can be connected or otherwise operatively coupled to one or both of the laser fiber 140 and the endoscope 110, such as to actuate lateral positioning of a distal portion of the laser fiber 140 within the longitudinal passage 145 or with respect to the endoscope 110. For example, the actuator 185 may include one or more of an electromagnetic element, an electrostatic element, a piezoelectric element, or other actuating element such as to actuate or otherwise permit lateral positioning of the laser fiber 140 with respect to the working channel or other longitudinal passage 145 of the endoscope 110 or with respect to another reference location for which the endoscope 110 can serve as a frame of reference.

Figure 1B:
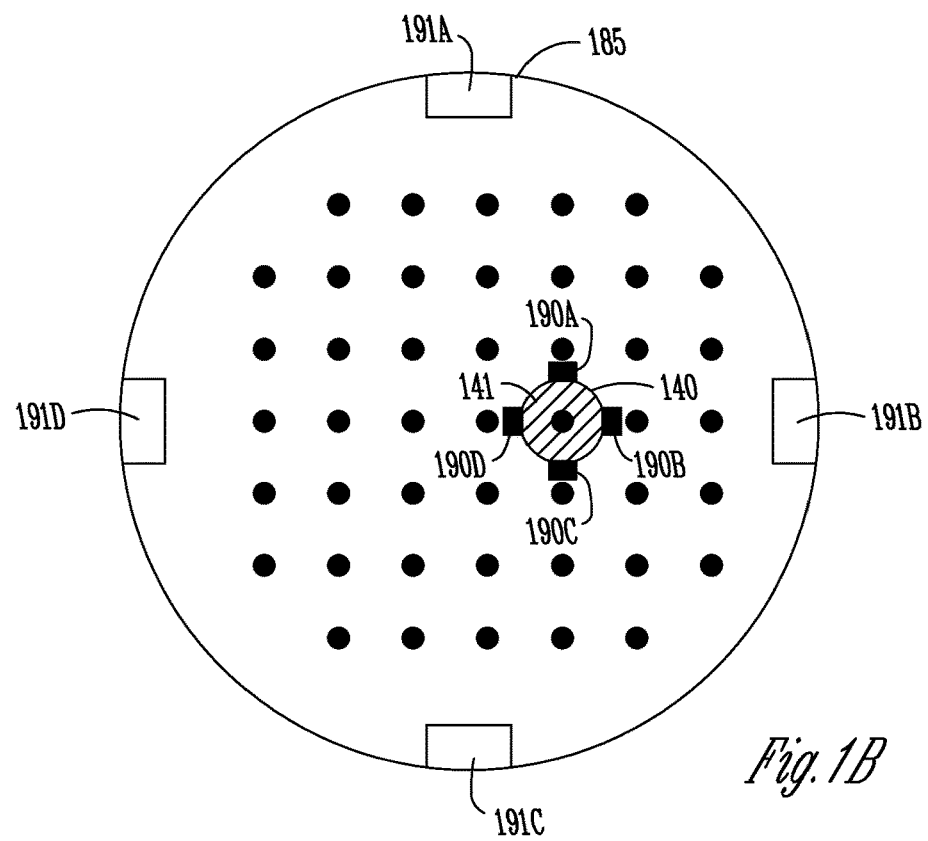

For example, FIG. 1B shows an end view of an example of a portion of the actuator 185, such as can be located within the longitudinal passage 145, such as can have a circular peripheral inner diameter. As shown in FIG. 1B, the actuator 185 can include at least one permanent magnet or electromagnet 190 such as can be affixed to a distal portion of the laser fiber 140. The one or more permanent magnets or electromagnets 190 can be influenced by a magnetic or electromagnetic field generated by the actuator 185. Such magnetic or electromagnetic field can be generated such as to actuate laterally positioning or re-positioning of the distal portion of the laser fiber 140 at one of a plurality of laterally displaced locations (which are illustrated conceptually in FIG. 1B by a dotted X-Y grid). Such magnetic or electromagnetic field can be generated via at least one permanent magnet or electromagnet 191 such as can be affixed at a desired location with respect to the longitudinal passage 145, such as within the longitudinal passage 145 or within a body of the endoscope 110 at or near the peripheral inner diameter of the longitudinal passage 145. Such magnetic or electromagnetic field influence can be used to laterally move the distal portion of the laser fiber 140 to a specified lateral position with respect to a fixed frame of reference of the endoscope 110, such as with respect to the longitudinal passage 145 of the endoscope 110.

Figure 1C:
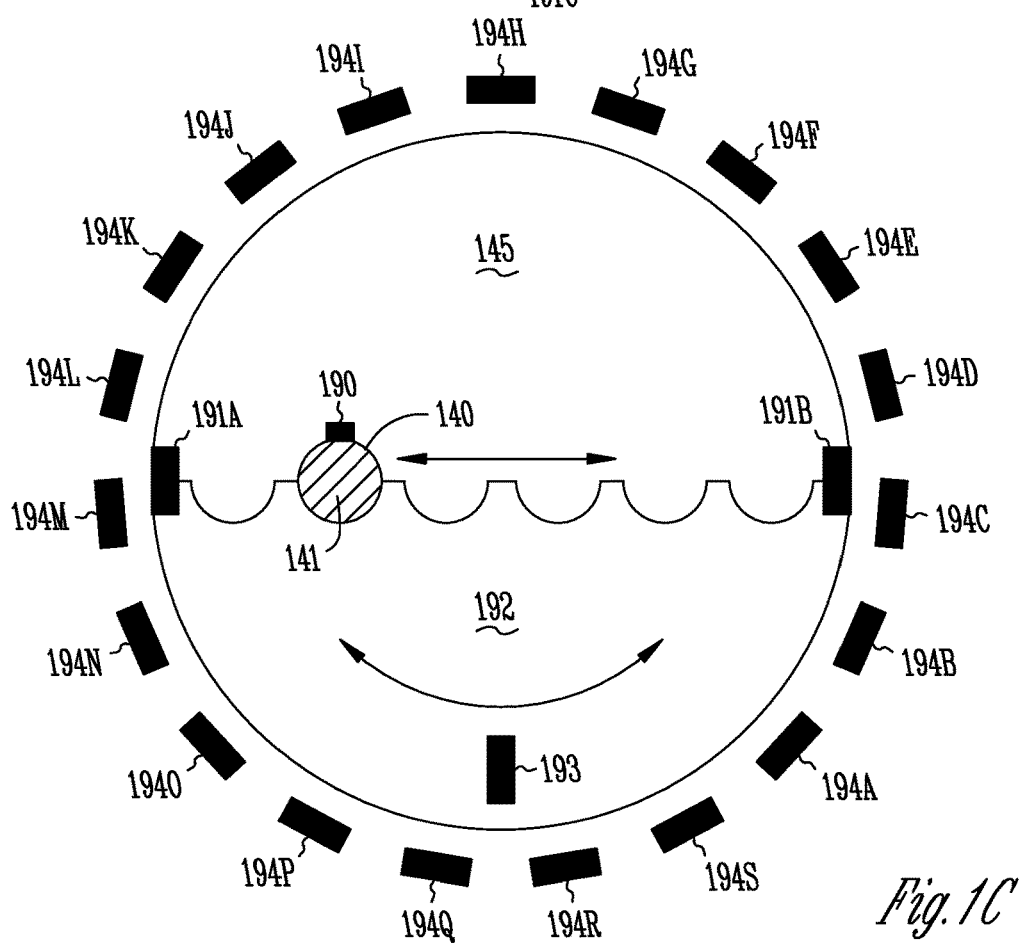

FIG. 1C shows an example of a portion of the actuator 185, in which 9283 such electromagnetic actuation of lateral movement or positioning can optionally be combined with and assisted by a mechanical stabilizer or positioning stage 192, for example, such as can include grooves or recesses such as can help provide multiple well-defined stable lateral locations at which the laser fiber 140 can "rest" when not being positioned or re-positioned electromagnetically by the actuator 185. For example, a linear series of grooves in a semi-circular disk shaped stabilizer stage 192, separated by well-defined specified distances, can define a series of available lateral positions at which the laser fiber 140 (or a secondary engagement mechanism) can be mechanically stabilized, and from which sub-targeted laser pulses can be emitted toward a target object. Such linear translation can be actuated by controlling the influence upon the permanent or electromagnet 190 (affixed to the laser fiber 140) by linear actuation permanent or electromagnets 191A-B such as can be located on the stage 192 toward the ends of the linear arrangement of available lateral positions. Rotational actuation of the mechanical stabilizer stage 192 by controlling the influence upon one or more permanent or electromagnets 193 affixed to the stage 192 by one or more permanent or electromagnets 194 that can be affixed to be distributed about the periphery of the longitudinal passage 145 can further provide rotational planar lateral positioning such as to permit sub-targeting by the laser fiber 140 in polar coordinates without requiring lateral repositioning of the endoscope 110. An X-Y arrangement of grooves in a stabilizer, separated by well-defined specified distances, can similarly define a planar matrix of available lateral positions for planar lateral positioning and sub-targeting in Cartesian coordinates. Illustrative examples of a secondary engagement mechanism or mechanical stabilizer or positioning stage 192 can include a pawl or a rack and pinion arrangement, among others.

The actuator 185 can additionally or alternatively use attractive or repulsive electrostatic forces, or both, between the distal portion of the laser fiber 140 and a fixed frame of reference provided by the endoscope 110, such as to laterally position or re-position the distal portion of the laser fiber 140 with respect to such fixed frame of reference. Such electrostatic actuation of lateral movement can optionally be combined with and assisted by a mechanical stabilizer or positioning stage 192, such as described herein.

The actuator 185 can additionally or alternatively use piezoelectric or ferroelectric material to impart force between the distal portion of the laser fiber 140 and a fixed frame of reference provided by the endoscope 110, such as to laterally position or re-position the distal portion of the laser fiber 140 with respect to such fixed frame of reference. Such piezoelectric or ferroelectric actuation of lateral movement can optionally be combined with and assisted by a mechanical stabilizer or positioning stage 192, such as described herein. The mechanical stabilizer or positioning stage 192 can optionally be part of a mechanical lithotripsy device that can be included or introduced in the endoscope 110, such as to deliver ultrasound or other mechanical impaction energy to a kidney stone or other stone or other target object. This can provide an additional lithotripsy modality, which can provide even further flexibility to the user for accomplishing a particular task or goal with respect to reduction or elimination or re-shaping of the target object.

In general, any actuator 185 capable of imparting force between the distal portion of the laser fiber 140 and a fixed frame of reference provided by the endoscope 110 is contemplated, alone, or optionally combined with a mechanical stabilizer or positioning stage. By configuring the actuator 185 to be remotely controlled, such as via the control circuitry 120, such lateral positioning or re-positioning of the distal portion of the laser fiber 140 can allow sub-targeting of multiple locations on a target object located near a distal end of the endoscope 110 or other instrument without requiring re-positioning of such endoscope 110 or other instrument. This can be useful to the user, who can keep the target object in view while such sub-targeting can be used to deliver a desired spatiotemporal series or sequence of laser pulses at various desired locations of the target object, including tailoring the energy level of one or more individual laser pulses. This can allow the user to deliver the desired energy to the desired locations in a desired spatial or spatiotemporal sequence, which, in turn, can help determine how the target object will ultimately fragment. By so doing, one or more desired fragmentation characteristics can be encouraged or obtained. This, in turn, can alleviate post-fragmentation tasks or complications.

The actuator 185 may be operated as a scanner, such as to direct the leading edge of the laser fiber 140 to an angle or direction according to an input voltage or other control signal. The actuator 185 can be controlled to direct the leading edge 141 of the laser fiber 140 to emit laser beam pulses along a specified spatial or spatiotemporal pattern (without requiring moving the endoscope 110), such as can include capability of adjusting the laser pulse energy intensity, such as on a pulse-by-pulse basis at one or more of such sub-targeting locations within the spatial or spatiotemporal pattern. In an example, the distance between such available sub-targeting locations can equal or exceed a diameter of the laser fiber 140. In another example, the distance between such sub-targeting locations can be less than the diameter of the laser fiber 140, such as can permit overlap in pulses delivered from adjacent sub-targeting locations among the plurality of available sub-targeting locations.

The laser source 130 can be configured to provide varying laser output via the laser fiber 140 toward the target object-such as can include continuous-wave laser output at low energy, such as for targeting, or pulsatile laser output, at adjustably variable higher energies. In an example, an initial positioning of the endoscope 110 and targeting using the laser source 130 can be used alone, or with other information. For example, such other information can be provided by a user via a user-interface, to establish one or more characteristics of the spatial or spatiotemporal pattern of sub-targeting one or more locations of the target stone or object. For example, by using the targeting or aiming laser beam provided by the laser source 130, the user can select the center of the target stone or object. Such target position information can be recorded by the control circuitry 120, and used to initiate an appropriate spatial or spatiotemporal pattern of sub-targeting one or more locations of the target stone or object, such as can be based at least in part on the initial user targeting of the center of the target stone or object. Similarly, the user can use the targeting laser beam provided by the laser source 130 to select the target center and one or more locations on the periphery of the target stone or object, and the control circuitry 120 can record such information and use such information to establish an appropriate spatial or spatiotemporal pattern of sub-targeting one or more locations of the target stone or object such as can be based at least in part on such initial user targeting of the center and periphery of the target stone or object. Other user input information or pre-operative or interoperative imaging information can be provided to the control circuitry 120, such as via one or more user interface devices or sensors, such as can provide information about one or more characteristics of the target stone or object or its environment. Such information can be used by the control circuitry 120, such as to select an appropriate spatial or spatiotemporal pattern of sub-targeting based on such single-dimensional or multi-dimensional information. Such selection can be algorithmic in nature, such as can involve weighting or blending information, or can use machine-learning or artificial intelligence techniques such as to select an appropriate spatial or spatiotemporal pattern of sub-targeting based on training data involving other target stones or objects or target environments manifesting one or more similar characteristics.

Figure 1D:
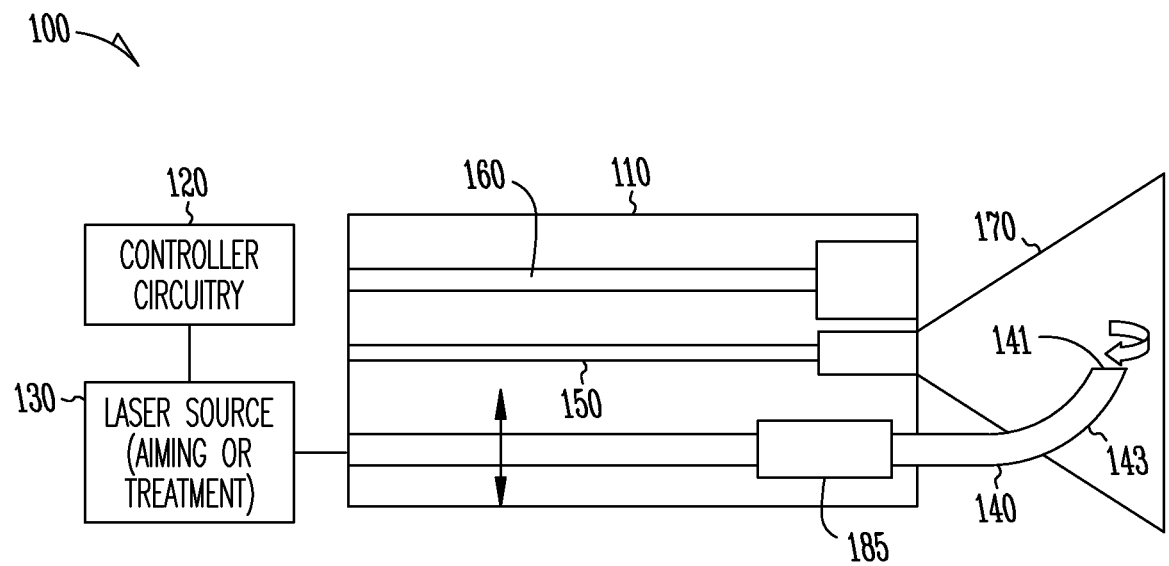

FIG. 1D illustrates an example in which the system 100 can include an optical fiber 140 that can include a distal portion such as can include an arcuate portion or other off-axis bend 143 or curve that can be directed at an angle from a central or other longitudinal axis of the endoscope 110. The bend 143 can be used alone or together with the lateral positioning provided by the actuator 185, such as to sub-target one or more locations within or even outside of a range defined by an inner diameter (ID) of the working channel or other longitudinal passage 145 or other lumen of the endoscope 110 through which the laser fiber 140 extends. Additionally or alternatively, the actuator 185 may optionally include rotational actuation capability, such as to rotate the bent distal portion of the laser fiber 140 for sub-targeting. The actuator 185 need not be located entirely at a distal portion of the endoscope 110. Instead, a portion of the actuator 185 may be located at the proximal handle 112 such as for rotating or vibrating the laser fiber 140, such as to obtain a desired orientation of a bent or straight distal portion of the laser fiber 140. Additionally or alternatively, the actuator 185 may optionally include bending actuation capability, such as to adjust the bend of the distal portion of the laser fiber 140 for sub-targeting, such as electromagnetically, electrostatically, piezoelectrically, or otherwise, such as explained herein. The sub-targeted locations, the sub-targeting peripheral boundary, or both can be additionally or alternatively controlled by one or more of such rotational actuation, bending actuation, or lateral actuation. Such variety of actuation may be useful during laser targeting (e.g., continuous wave) or laser treatment (e.g., pulsed), such as explained herein, and need not require moving the endoscope 110 or the laser source 130.

Figure 1E:
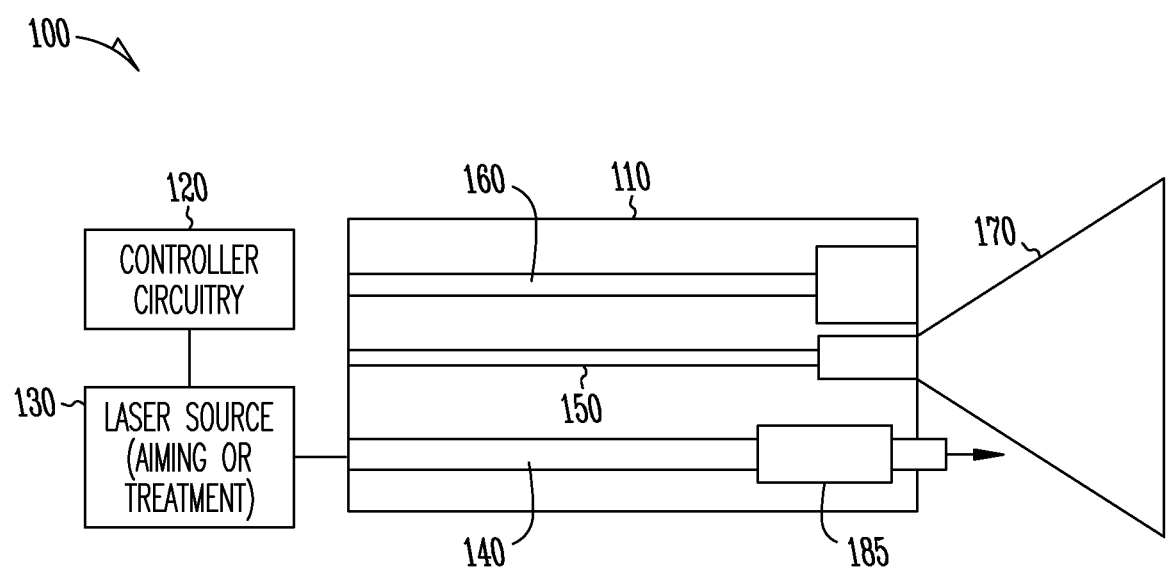
Figure 1F:
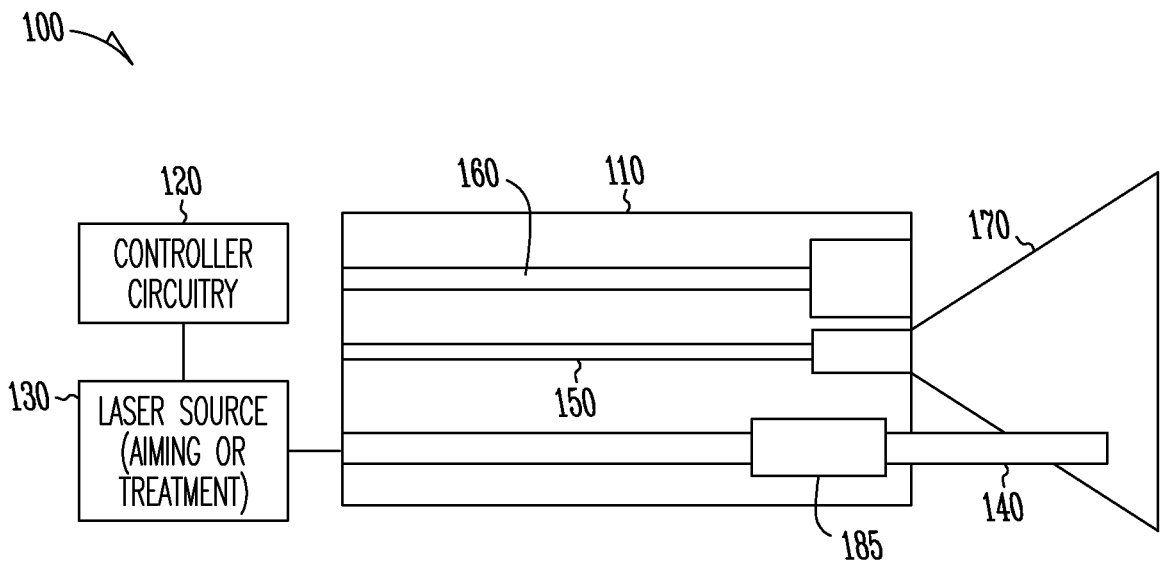
Figure 1G:
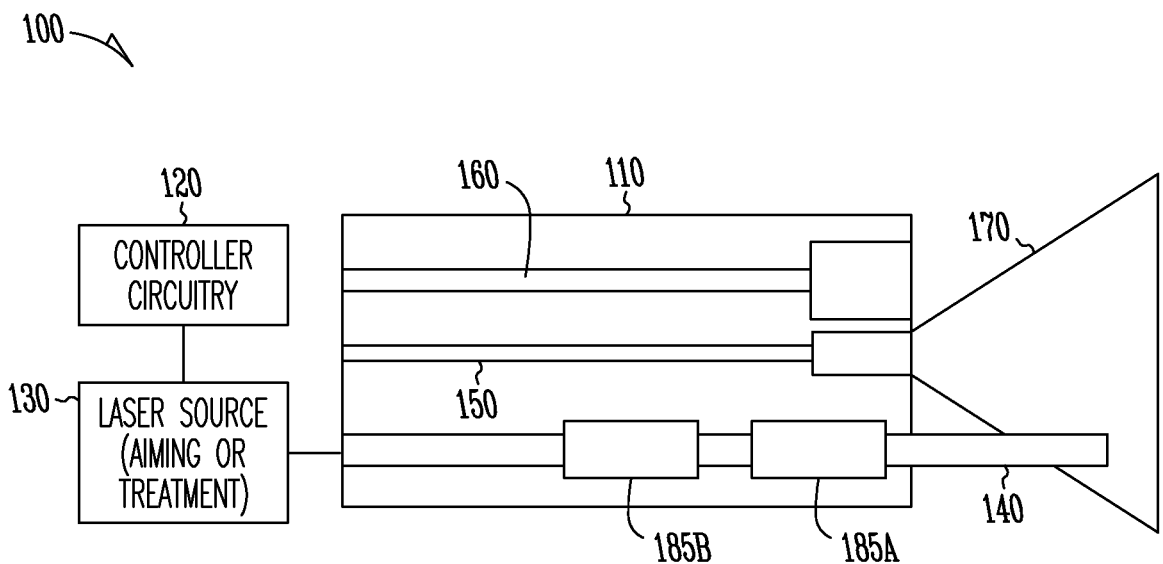

FIGS. 1E and 1G show an example of the system 100 in which the laser fiber 140 can be longitudinally axially translated to various positions with respect to a distal end of the endoscope 110. As shown in FIGS. 1E and 1F, such axial translation of the laser fiber 140 can include longitudinal axial translation (e.g., sliding) with respect to the actuator 185. This can permit the actuator 185 to remain within the endoscope 110, such as to provide the lateral positioning or re-positioning of the laser fiber 140, while still allowing freedom of re-positioning the laser fiber 140 axially, such as can include protruding outward from a distal end of the working channel or other lumen of the endoscope 110, or such as can include being retracted to be even with or drawn slightly within the working channel or other longitudinal passage 145 or lumen of the endoscope 110. Regardless of the axially translated position of the distal face 141 of the laser fiber 140, the laser fiber 140 may still be adjustably positioned laterally with respect to the longitudinal passage 145 or other fixed frame of reference of the endoscope 110. The lateral positioning of the distal portion of the laser fiber 140 can be selected from a plurality of available laterally positions (e.g., such as shown by the dotted grid of FIG. 1B). The lateral movement of the laser fiber 140 can be conducted without movement of the endoscope 110 or the laser source 130. FIG. 1E shows an example in which the distal face 141 of the laser fiber 140 can be longitudinally translated and positioned to extend out of the endoscope 110 and into the body, for example, to accomplish positioning of the laser fiber 190 to the desired site of treatment.

In some examples, more than one actuators may be used to respectively actuate and control different motions of the laser fiber 140. FIG. 1G illustrates an example of the system 100 that comprises two separate actuators in the endoscope. In the example as illustrated therein, a first actuator 185A can control an longitudinal axial translation of the laser fiber 140, and a different second actuator 185B can control a lateral positioning of the laser fiber 140.

Figure 1H:
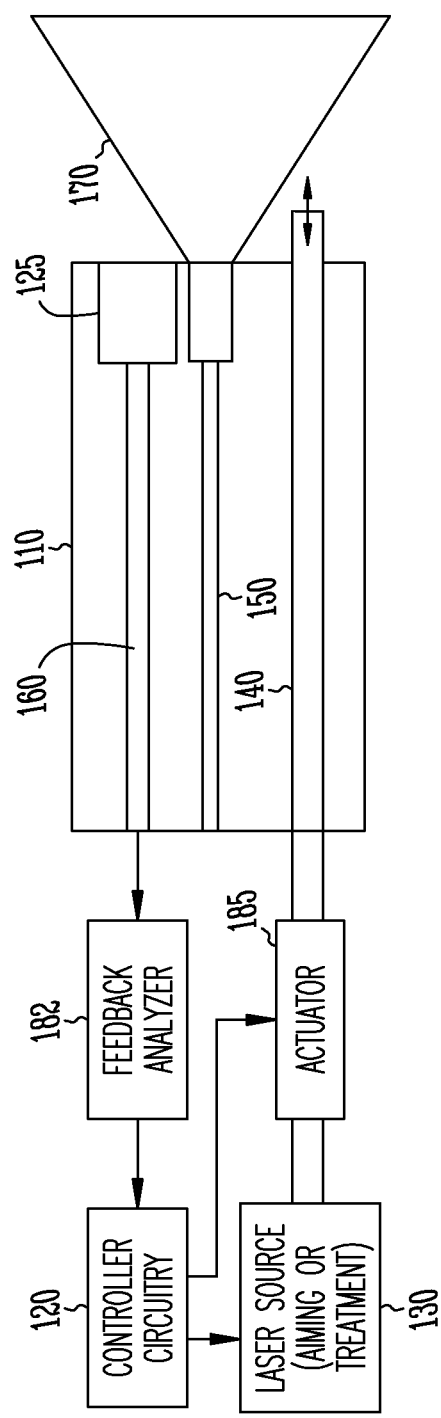
Figure 1I:
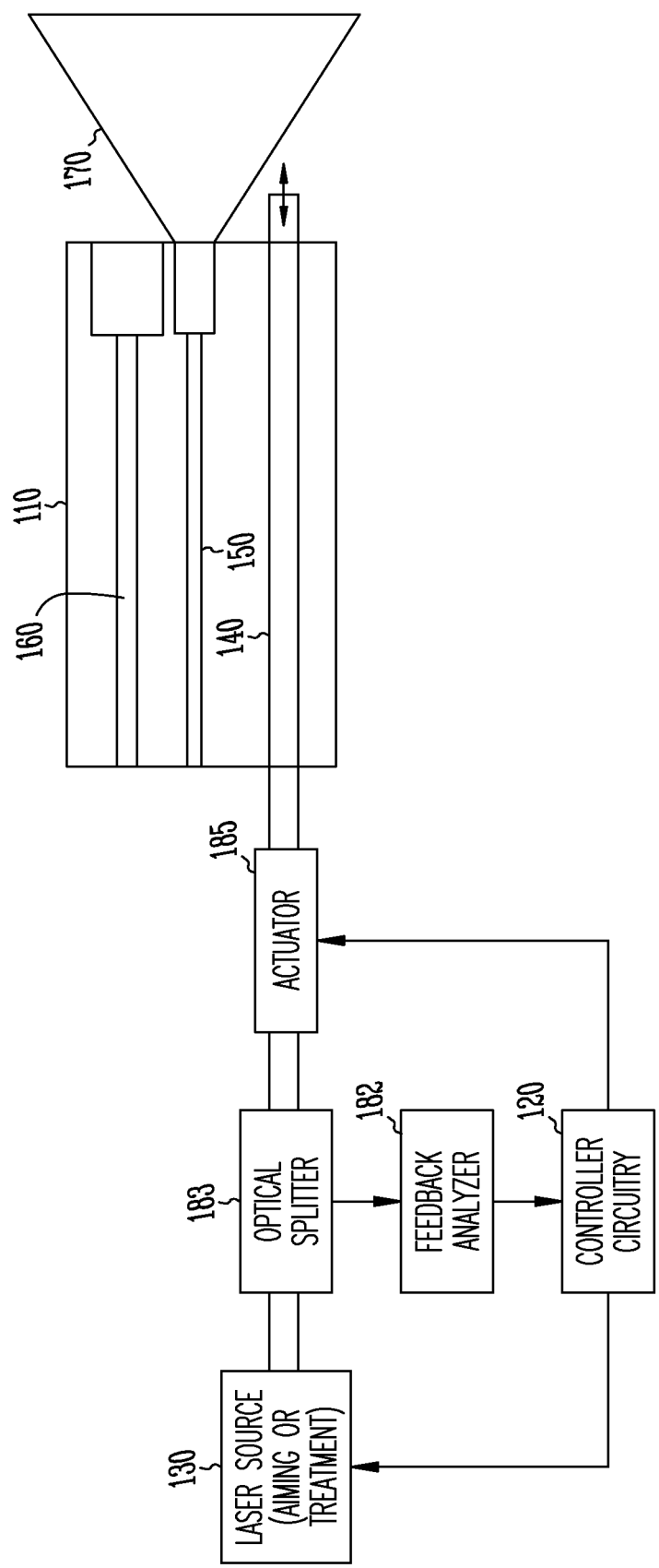

FIGS. 1H and 1I illustrate examples of the system 100 that uses a feedback signal reflected from the target to control and adjust the position of the laser fiber 140 with respect to a distal end of the endoscope 110. The feedback signal may be produced in response to electromagnetic radiation of the target (e.g., the light 170). In FIG. 1H, the target is within the view of an endoscopic camera or imaging device 125 through the optical pathway 160. In response to electromagnetic radiation of the target, signal reflected from the target may be collected by the endoscopic camera or imaging device 125. Imaging data of the target can be transmitted through the optical pathway 160 to a feedback analyzer 182. The feedback analyzer 182 may include a spectrometer configured to generate one or more spectroscopic properties from the imaging data. The controller circuitry 120 can adjust laser settings of the laser source 130 using the one or more spectroscopic properties. The feedback analyzer 182 may additionally calculate a distance between the distal end of the laser fiber 140 and the target. The controller circuitry 120 can control the actuator 185 to adjust the position of the fiber distal end based on the calculated distance between the distal end of the laser fiber 140 and the target. For example, if the calculated distance exceeds a desired laser firing range (within a specified margin), then the controller circuitry 120 may generate a control signal to the control the actuator 185 to slide the laser fiber 140 towards the target until the fiber distal end reaches within the laser firing range with respect to the target. In some examples, spectroscopic information of the target from the feedback analyzer 182 may be used by the controller circuitry 120 to determine movement and position of laser fiber 140 via the actuator 185.

In addition to or in lieu of transmitting an imaging signal from through the optical pathway 160, in some examples, the signal reflected from the target may be collected and transmitted through a separate optical pathway. In FIG. 1I, the laser fiber 140 may be used for delivering laser beams to the target and for transmitting spectroscopic data of the target back to the feedback analyzer 182. An optical splitter 183 can direct the reflected feedback signal to the feedback analyzer 182. The feedback analyzer 182 may generate one or more spectroscopic properties from the spectroscopic signal, and the controller circuitry 120 can adjust laser settings of the laser source 130 using the one or more spectroscopic properties. Similar to the discussion above with reference to FIG. 1H, the feedback analyzer 182 may additionally calculate a distance between the distal end of the laser fiber 140 and the target. The controller circuitry 120 can control the actuator 185 to adjust the position of the fiber distal end based on the calculated distance, optionally along with the spectroscopic information of the target from the feedback analyzer 182.

Figure 2:
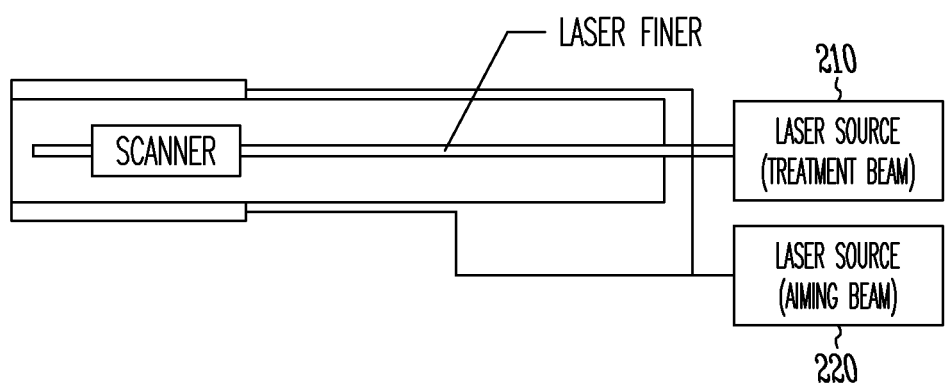
FIG. 2 illustrates a side sectional view of portions of an endoscope system.

FIG. 2 illustrates an example of portions of a system 200, similar to system 100, in which the laser source 130 can include a combination of two laser sources, such as can include a treatment laser source 210 such as can provide a treatment laser beam (e.g., pulsed, higher energy) and an aiming laser source 220 such as can provide an aiming beam (e.g., continuous wave, lower energy). The treatment beam 210 may include laser pulses of adjustable or variable energy. For example, lower energy pulses can be used to first form cracks on a target surface of a stone or other target, such as according to a desired or specified spatial or spatiotemporal pattern. Then, one or more higher energy pulses can be used to fragment the stone or other target, such as can be biased toward tending to fragment along the previously established cracks. By so doing, the morphology of the resulting fragments can be better controlled.

In an example, the treatment beam may include laser energy that can be delivered at variable peak power, instead of or in addition to delivering laser pulses of adjustable or variable energy. For example, instead of delivering laser energy at a particular pulse width and constant amplitude, the pulse width can be increased by a factor and the amplitude decreased by the same factor so that the same amount of laser energy can be delivered at a different power level. Variable energy and variable power can be used together or separately in a sequence of laser pulses such as can be delivered according to a desired spatiotemporal pattern to a target region. For example, low peak power with long pulse width can help vaporize organic or inorganic substances in a target stone (e.g., for calcium oxalate monohydrate crystal, delivering laser energy at a lower temperature can help the energy penetrate to a greater depth) such as to help accelerate thermal degradation of the target stone. Following delivery of laser energy at a lower peak power (e.g., with long pulse widths) laser energy can then be delivered at higher peak power, shorter pulse width to create thermal gradient in the target stone, if desired.

Figure 3:
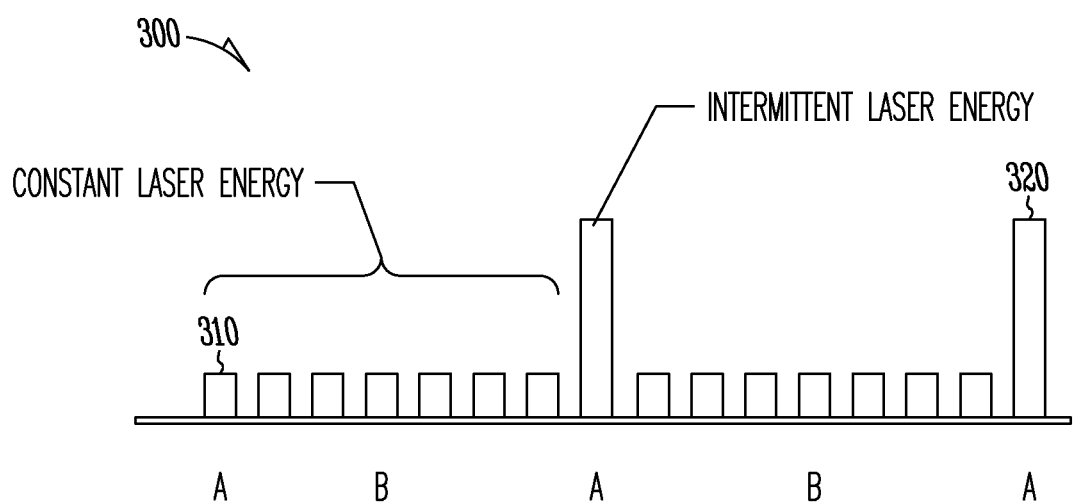
FIG. 3 illustrates a graph of using different laser energies.

FIG. 3 illustrates a spatiotemporal graph 300 of using a spatiotemporal sequence of laser pulses having different pulsed energy or power levels, such as can include lower energy pulses 310 and higher energy laser pulses 320. In FIG. 3, the sequence represents time in the X-direction of the graph, but is also annotated with locations "A" and "B" on the stone or other target. In this example, location "A" is at or near the center of the stone or other target, and location "B" is at or near a periphery of the stone or other target. The laser pulses issued between locations "A" and "B" illustrate pulses that are issued as the laser fiber 140 is being translated from the location "A" to the location "B", or as the laser fiber 140 is being translated from the location "B" to the location "A", such as can include using the actuator 185. The lower energy pulses 310 can be selected to induce a crack in the target stone without fragmenting the target stone. Thus, in FIG. 3, such lower energy pulses 310 can be issued beginning at location "A" toward the center of the stone, then proceeding toward location "B" toward a periphery of the stone, and then returning toward location "A" at the center of the stone, at which time a higher energy pulse 320 can be delivered in a first attempt to fragment the target stone. If such fragmenting by the higher energy pulse 320 is not successful, then further lower energy pulses 310 can be delivered proceeding from locations toward the center of the stone toward a location "B" toward the periphery of the stone, and then returning toward location "A" at the center of the stone, at which time another higher energy pulse 320 can be delivered in a second attempt to fragment the target stone. Further iterations are also possible. The same or a different location "B" toward the periphery of the stone can be used for the various iterations, with different locations "B" in different iterations producing multiple cracks along such pathways from location "A" to such different peripheral location "B". It may be preferred to use the higher energy pulse 320 only toward the center of the stone, such as to minimize the effect of the higher energy pulses 320 on nearby tissue. The spatiotemporal pattern shown in FIG. 3 is an illustrative example of one such pattern that can be obtained, such as using the actuator 185, such as can be remote-controlled using the control circuitry 120, such as explained above.

FIG. 4A-4D show examples of spatial or spatiotemporal patterns such as can be obtained using the actuator 185, such as can be remotely controlled using the control circuitry 120, without requiring re-positioning of the endoscope 110 by the user. As explained herein, such lateral positioning actuation of the laser fiber 140 can be accompanied by rotational positioning actuation, such as to provide sub-targeting such as according to polar coordinates.

Figure 4A:
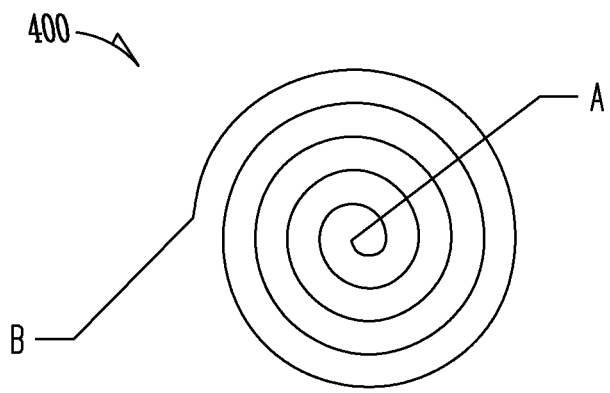
FIGS. 4A-4D illustrates various examples of a varying spatial or spatiotemporal locus of laser beam such as can be laterally actuated without requiring moving an endoscope.

In FIG. 4A, lower energy laser pulses may be issued beginning from a peripheral location "B" at the periphery of the target stone B, and such pulses may be applied along a spiral path 410 toward a central location "A", at which a higher energy pulse can be issued in an attempt to fragment the pre-cracked or pre-weakened target stone after its treatment by the lower energy pulses. Multiple iterations are possible, such as explained herein, such as can also optionally vary one or more of energy or power levels.

Figure 4B:
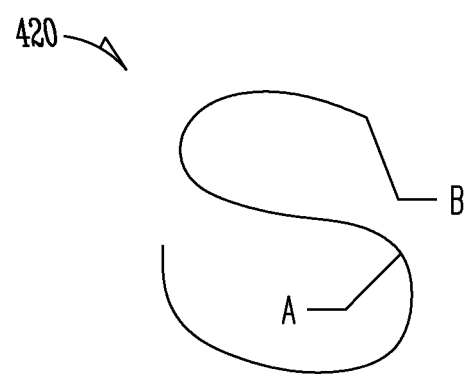

In FIG. 4B, lower energy laser pulses may be issued beginning at a peripheral location "B" and may proceed to be issued along a serpentine path 420. A higher energy laser pulse "A" may be applied at or near a central location "A" of the target stone, either on an initial path, of after completion of the serpentine path. Further iterations are possible, such as explained herein, such as can begin at or near the same or a different peripheral location "B", such as can also optionally vary one or more of energy or power levels.

Figure 4C:
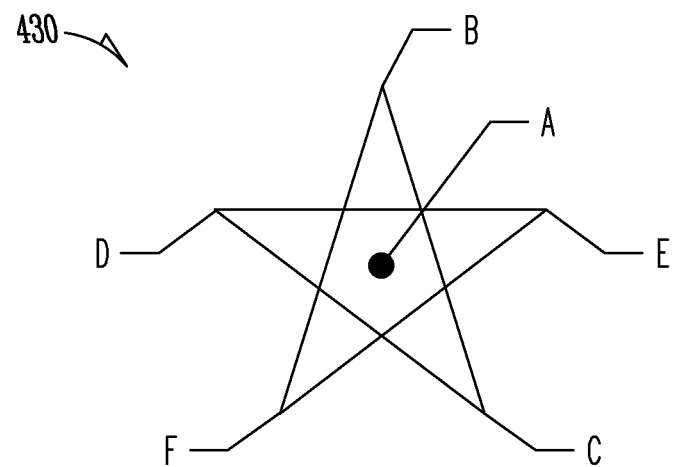

In FIG. 4C, lower energy laser pulses may be issued beginning at a peripheral location "B" and may proceed to be issued along a "star" path of linear segments, such as proceeding from peripheral location "B" to peripheral location "C" to peripheral location "D" to peripheral location "E" to peripheral location "F" to peripheral location "B". Then, a higher energy laser pulse may be issued and directed toward center location "A".

Figure 4D:
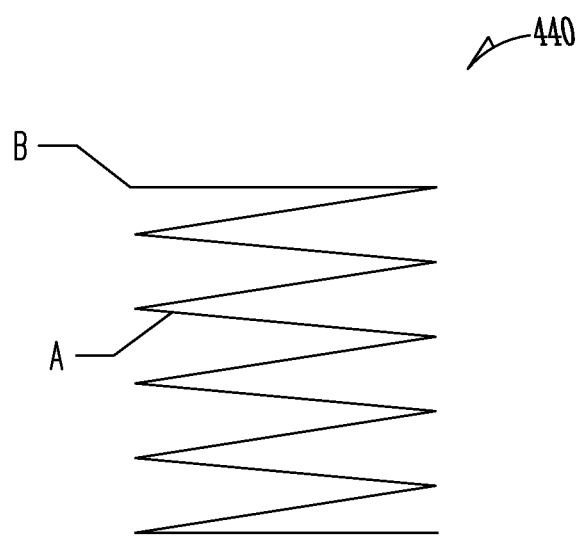

In FIG. 4D, lower energy laser pulses may be issued beginning at a peripheral location "B" and may proceed along a zig-zag pattern 440 across the target stone. Then, a higher energy laser pulse may be issued and directed toward a center location "A". Further iterations are possible, such as explained herein, such as can begin at or near the same or a different peripheral location "B", such as can also optionally vary one or more of energy or power levels.

The above description has emphasized a use-case involving lithotripsy via an endoscopic instrument. However, the present techniques can also be applied using other minimally-invasive instruments (e.g., a laparoscope, arthroscope, or the like) or even using a guide in open-surgery. The present laser sub-targeting without requiring moving of the guide device can also be used with medical treatment techniques other than lithotripsy, or for laser surgery or other uses involving targeted delivery of laser energy. The target can include not only a kidney stone, biliary stone, gall bladder stone, or other stone, but also to bone or cartilage or other hard or soft tissue.

In a tissue ablation example in which the target includes tissue to be ablated or coagulated, instead of a target stone a desired spatiotemporal pattern can include providing fixed or variable energy, fixed or variable power, or fixed or variable wavelength laser energy from one or more laser sources such as in pulsatile, continuous wave, or other manner, such as to promote one or more of cutting or coagulation, or to balance or otherwise coordinate between these two or other objectives.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. 821 In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A laser therapy system to permit delivering therapeutic laser energy from different lateral positions, the laser therapy system comprising:
    an endoscope defining a longitudinal passage;
    an optical fiber, including a distal portion that is configured to be inserted into a patient via the longitudinal passage of the endoscope,
    at least one actuator, the at least one actuator configured to controllably actuate the distal portion of the optical fiber to be adjustably positioned, at least laterally, within the longitudinal passage at a selected position of a plurality of laterally displaced positions within the longitudinal passage of the endoscope, wherein the adjustably positioned optical fiber is configured to direct therapeutic laser energy to the patient; and
    a stabilizer stage within the longitudinal passage, the stabilizer stage including, at the plurality of laterally displaced positions, a plurality of grooves or recesses each shaped to receive and stabilize the distal portion of the optical fiber after being positioned by the at least one actuator.

2. The system of claim 1, wherein the distal portion of the optical fiber includes a bend.

3. The system of claim 2, wherein the at least one actuator is configured to controllably actuate a rotation of the distal portion of the optical fiber about the longitudinal passage.

4. The system of claim 1, comprising: a laser source coupled to the optical fiber; and controller circuitry configured to control the laser source to provide first and second laser pulses via the optical fiber coupled to the laser source, wherein the second laser pulse includes a higher energy than the first laser pulse, wherein the second pulse is issued laterally closer to a center of a target than when the first laser pulse is issued without requiring lateral repositioning of the endoscope.

5. The system of claim 1, wherein the at least one actuator is configured to actuate lateral displacement of the distal portion of the optical fiber in a specified pattern according to a control signal provided by controller circuitry.

6. The system of claim 5, wherein the at least one actuator is configured to controllably actuate a longitudinal translation of the distal portion of the optical fiber with respect to the at least one actuator.

7. The system of claim 5, wherein the at least one actuator comprises: a first actuator configured to actuate lateral displacement of the distal portion of the optical fiber; and a different second actuator configured to actuate longitudinal translation of the optical fiber.

8. The system of claim 5, comprising the controller circuitry that is configured to generate the control signal for actuating the at least one actuator using a feedback signal in response to electromagnetic radiation of a target.

9. The system of claim 8, wherein the feedback signal includes imaging data or spectroscopic data.

10. The system of claim 8, wherein the controller circuitry is configured to generate the control signal for actuating the at least one actuator using information about a distance between a distal end of the optical fiber and the target.

11. The system of claim 5, wherein the at least one actuator is configured to actuate the distal portion of the optical fiber to be adjustably positioned, at least laterally, within the longitudinal passage at a selected position of a plurality of laterally displaced positions within the longitudinal passage of the endoscope while maintaining the endoscope laterally stationary.

12. The system of claim 11, wherein the at least one actuator is located at the distal portion of the optical fiber.

13. The system of claim 11, wherein the at least one actuator is located at a proximal portion of the optical fiber.

14. The system of claim 1, wherein the distal portion of the optical fiber is at least electromagnetically actuatable to be laterally displaced within the longitudinal passage when actuated in accordance with a control signal provided by controller circuitry.

15. The system of claim 1, comprising: a laser source coupled to the optical fiber; and controller circuitry configured to control the laser source to provide a lateral pattern of lower energy laser pulses toward a periphery of a target and at least one higher energy laser pulse toward a center of the target, without requiring lateral repositioning of the endoscope.

16. The system of claim 15, wherein the lateral pattern includes at least one of a spiral pattern, a serpentine pattern, a star pattern, or a zig-zag pattern.

17. The system of claim 1, wherein the at least one actuator is configured to controllably actuate the distal portion of the optical fiber to be adjustably positioned at least laterally positioned within the longitudinal passage and with respect to a central longitudinal axis of the longitudinal passage at a selected position of a plurality of laterally displaced positions within the longitudinal passage of the endoscope.

18. The system of claim 1, wherein the at least one actuator is configured to controllably actuate the distal portion of the optical fiber to be adjustably at least laterally positioned within the longitudinal passage and with respect to a central longitudinal axis of the optical fiber at a selected position of a plurality of laterally displaced positions within the longitudinal passage of the endoscope.

19. The system of claim 1, wherein the at least one actuator further includes one or more magnetic or electromagnetic elements affixed to a distal portion of the optical fiber.

20. The system of claim 1, further comprising at least one of 1) an illumination optic extending from a proximal portion of the endoscope to a distal portion, and coupled to a proximal illumination light source, or 2) a distal illumination light source coupled to the distal portion of the endoscope.

21. A method of delivering therapeutic laser energy via an endoscope to permit at least laterally re-orienting a laser beam with respect to a target region without requiring moving the endoscope, the method comprising:

providing an optical fiber configured to extend through a longitudinal passage of the endoscope, and to deliver the therapeutic laser energy produced by a laser source;

issuing or receiving a control signal to actuate, via at least one actuator, positioning of a distal portion of the optical fiber at least laterally within the longitudinal passage of the endoscope at a selected position of a plurality of laterally displaced positions within the longitudinal passage of the endoscope; and receiving and stabilizing, via a stabilizer stage within the longitudinal passage, the distal portion of the optical fiber into one of a plurality of grooves or recesses of the stabilizer stage located at the plurality of laterally displaced positions after being positioned by the at least one actuator.

22. The method of claim 21, wherein the optical fiber is actuated by a controller to provide first and second laser pulses from the laser source via the optical fiber, wherein the second laser pulse includes a higher energy than the first laser pulse.

23. The method of claim 22, wherein the second laser pulse is issued when the distal portion of the optical fiber is relatively closer to a center of the target region than when the first laser pulse is issued, without requiring lateral repositioning of the endoscope.

24. The method of claim 22, wherein the second laser pulse is issued after a specified time interval of when the first laser pulse is issued, and wherein the first laser pulse is issued repeatedly to consistently apply a first laser pulse energy to a targeted region.

25. The method of claim 24, wherein the first laser pulse is issued repeatedly while directed along a pattern boundary toward a lateral periphery of a target region, wherein the second laser pulse is applied laterally closer to a center of the target region.

26. The method of claim 21, wherein the distal portion of the optical fiber is laterally displaced in a spiral pattern according to a control signal provided by a controller.

27. The method of claim 21, wherein the distal portion of the optical fiber is laterally displaced in a serpentine pattern according to a control signal provided by a controller.

28. The method of claim 21, wherein the distal portion of the optical fiber is laterally displaced in a zig-zag pattern according to a control signal provided by a controller.

29. The method of claim 21, wherein the distal portion of the optical fiber is laterally displaced in a star pattern according to a control signal provided by a controller.

30. The method of claim 21, further comprising using information about at least one of a morphology or a composition of at least a portion of the target region to select or control a target pattern including different targeted lateral positions.

31. The method of claim 21, further comprising issuing or receiving a control signal to actuate the distal portion of the optical fiber to be laterally displaced in a specified pattern to issue one or more laser pulses toward a lateral periphery of a target region before issuing one or more laser pulses closer to a center of the target region.

32. The method of claim 21, further comprising providing at least one of: 1) an illumination optic extending from a proximal portion of the endoscope to a distal portion, and coupled to a proximal illumination light source, or 2) a distal illumination light source coupled to the distal portion of the endoscope.

33. A laser therapy system for delivering therapeutic laser energy to permit at least laterally re-orienting a laser beam toward a target, the system comprising:

an endoscope defining a longitudinal passage;

an optical fiber configured to extend through the longitudinal passage of the endoscope, means for issuing or receiving a control signal to actuate at least one actuator, to adjustably position a distal portion of the optical fiber at a selected position of a plurality of laterally displaced positions within the longitudinal passage of the endoscope; and means for receiving and stabilizing the distal portion of the optical fiber into one of a plurality of grooves or recesses at the plurality of laterally displaced positions after being positioned by the at least one actuator.

34. The system of claim 33, comprising: a laser source coupled to the optical fiber; and controller circuitry configured to provide first and second laser pulses via the optical fiber, wherein the second laser pulse includes a higher energy than the first laser pulse, wherein the second pulse is issued laterally closer to a center of the target than when the first laser pulse is issued, without requiring lateral repositioning of the endoscope.

35. The system of claim 33, further comprising at least one of 1) an illumination optic extending from a proximal portion of the endoscope to a distal portion, and coupled to a proximal illumination light source, or 2) a distal illumination light source coupled to the distal portion of the endoscope.

* * * * *

UNITED STATES PATENT AND TRADEMARK OFFICE
CERTIFICATE OF CORRECTION

PATENT NO. : 12,279,812 B2  
APPLICATION NO. : 16/984440  
DATED : April 22, 2025  
INVENTOR(S) : Shelton et al.

Page 1 of 1

It is certified that error appears in the above-identified patent and that said Letters Patent is hereby corrected as shown below:

In the Claims

In Column 15, Line 31, in Claim 1, delete "endoscope," and insert --endoscope;-- therefor In Column 17, Line 6, in Claim 21, delete "endoscope," and insert --endoscope-- therefor In Column 18, Line 25, in Claim 33, delete "endoscope," and insert --endoscope;-- therefor Signed and Sealed this
Fifth Day of August, 2025

Coke Morgan Stewart
*Acting Director of the United States Patent and Trademark Office*